United States Patent
Brown

(10) Patent No.: US 12,217,868 B2
(45) Date of Patent: Feb. 4, 2025

(54) DIFFERENTIAL DIAGNOSIS FEATURE ENGINEERING FOR MACHINE LEARNING APPLICATIONS

(71) Applicant: Red Hat, Inc., Raleigh, NC (US)

(72) Inventor: Douglas Graeme Brown, Hobart (AU)

(73) Assignee: Red Hat, Inc., Raleigh, NC (US)

( * ) Notice: Subject to any disclaimer, the term of this patent is extended or adjusted under 35 U.S.C. 154(b) by 657 days.

(21) Appl. No.: 17/389,583

(22) Filed: Jul. 30, 2021

(65) Prior Publication Data
US 2023/0036102 A1 Feb. 2, 2023

(51) Int. Cl.
G16H 50/20 (2018.01)
G06F 21/55 (2013.01)
G06N 20/00 (2019.01)
G16H 50/70 (2018.01)

(52) U.S. Cl.
CPC ........... *G16H 50/20* (2018.01); *G06F 21/554* (2013.01); *G06N 20/00* (2019.01); *G16H 50/70* (2018.01)

(58) Field of Classification Search
None
See application file for complete search history.

(56) References Cited

U.S. PATENT DOCUMENTS

| | | |
|---|---|---|
| 7,594,270 B2 | 9/2009 | Church et al. |
| 10,847,265 B2 | 11/2020 | Kannan et al. |
| 2013/0054642 A1* | 2/2013 | Morin ................ G06F 16/258 |
| | | 707/E17.014 |
| 2020/0057850 A1 | 2/2020 | Kraus et al. |
| 2020/0410001 A1* | 12/2020 | Sarkissian ............. G06F 3/0482 |
| 2022/0100868 A1* | 3/2022 | Tarrant .................. G06N 20/00 |

OTHER PUBLICATIONS

How to Start Security Automation with Exabeam; https://www.exabeam.com/customers/; 2021; retrieved Mar. 4, 2020 (15 pages).
IBM's Watson supercomputer recommended 'unsafe and incorrect' cancer treatments, internal documents show; Casey Ross et al.; Jul. 25, 2018; https://www.statnews.com/2018/07/25/ibm-watson-recommended-unsafe-incorrect-treatments/; retrieved Jul. 29, 2021; 2 pages.

* cited by examiner

*Primary Examiner* — Syed A Roni
(74) *Attorney, Agent, or Firm* — Kilpatrick Townsend & Stockton LLP

(57) ABSTRACT

Methods and systems for improved preparing of received data using differential diagnosis for analysis by machine learning models. In one embodiment, a method is provided that includes receiving an identifier of an event. A plurality of inquiries may be sequentially processed, and subsequent inquiries for processing may be selected based on the responses to earlier inquiries. A tensor may be used to store indications of which inquiries were processed and the responses received to the inquiries. A machine learning model may use the tensor to determine a diagnosis and whether the event is an emergency event requiring intervention. If the event is an emergency event, an intervention may be generated for the emergency event, which may include a computer system taking automatic action to respond to the emergency event.

20 Claims, 7 Drawing Sheets

DIFFERENTIAL DIAGNOSIS FEATURE ENGINEERING FOR MACHINE LEARNING APPLICATIONS

BACKGROUND

In various environments, information may be received regarding events or situations that require immediate or near-immediate responses from one or more individuals. For example, emergency medical situations may require immediate intervention by one or more medical professionals in order to prevent a negative medical outcome for a patient. As another example, computer security systems may be breached or otherwise compromised, and indications of such computer security events may require immediate action by computer security analysts to intercept or otherwise prevent security compromises.

SUMMARY

The present disclosure presents new and innovative systems and methods for preparing received data using differential diagnosis for analysis by machine learning models. In a first embodiment, a method is provided that includes receiving an identifier of a computer system security event and sequentially processing a plurality of inquiries. Subsequent inquiries in the plurality of inquiries may be selected and asked based on responses to earlier inquiries in the plurality of inquiries. Indications of (i) the plurality of inquiries processed and (ii) responses received to the plurality of inquiries may be stored into a tensor and a machine learning model may be used to determine that the tensor identifies a potential computer system security breach. The method may also include generating an intervention for the potential computer system security breach.

In a second embodiment, a system is provided that includes a processor and a memory. The memory may store instructions which, when executed by the processor, cause the processor to receive an identifier of a medical event and sequentially process a plurality of inquiries. Subsequent inquiries in the plurality of inquiries may be selected and asked based on responses to earlier inquiries in the plurality of inquiries. The instructions may also cause the processor to store indications of (i) the plurality of inquiries processed and (ii) responses received to the plurality of inquiries into a tensor and determine, with a machine learning model, that the tensor identifies a potential medical diagnosis. The instructions may further cause the processor to generate an intervention for the potential medical diagnosis.

The features and advantages described herein are not all-inclusive and, in particular, many additional features and advantages will be apparent to one of ordinary skill in the art in view of the figures and description. Moreover, it should be noted that the language used in the specification has been principally selected for readability and instructional purposes, and not to limit the scope of the disclosed subject matter.

DETAILED DESCRIPTION OF EXAMPLE EMBODIMENTS

Figure 1:
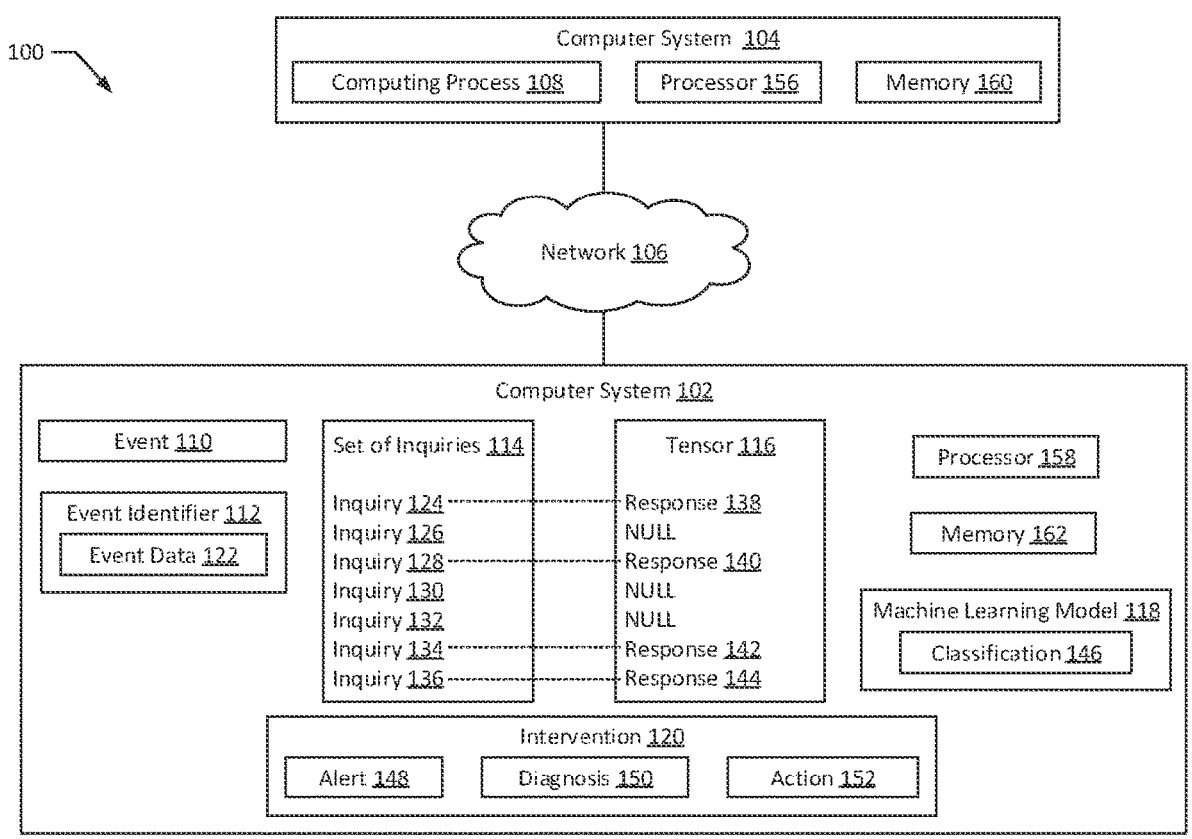
FIG. 1 illustrates a system for differential diagnosis feature engineering according to an exemplary embodiment of the present disclosure.

Triaging received alerts of urgent events often requires synthesizing multiple, disparate sources of information. In particular, analysts may need to consult additional contextual information to determine when indications require immediate intervention. For example, when a medical professional receives an indication of a medical event, the medical professional may consult recent imaging or measurements of vitals for an associated patient. As another example, when a computer security professional receives indications of a potential computer security breach, the computer security professional may consult additional information regarding traffic on an associated computing network.

As organizations expand, the volume of alerts may also continue to grow and expand. This growth in alerts also increases the number of alerts that require close scrutiny by analysts. Such alerts can consume significant amounts of time for analysts tasked with identifying urgent events. For example, computer security analysts may be required to spend a significant amount of time analyzing incoming alerts for potential computer security breaches. As another example, medical professionals may be required to spend a significant amount of time processing alerts for incoming medical events.

Therefore, there exists a need to automatically process received alerts to identify events (e.g., medical events, computer security events) that require immediate intervention. However, automating this analysis is not trivial, and quite different than simply automating how a human deals with the same data. First, different types of alerts or diagnoses require different analytical techniques to identify when the analysis is automated; one cannot simply apply the same approach to all kinds of alerts or diagnoses. For example, identifying a distributed denial of service (DDoS) attack requires different analytical techniques (and corresponding information sources) than a compromised user account. In practice, alerts may be received for hundreds or thousands of different types of potential events, and each different type may require a different analysis to properly determine whether an alert identifies such an emergency event (e.g., a particular security breach, a particular diagnosis). Moreover, the number of alerts may be far greater than a human could even review in a reasonable amount of time, even just to determine which sort of analysis is required. Accordingly, it is not feasible to prepare separate machine learning models and/or separate heuristic techniques for each type of potential event. Furthermore, training machine learning models to process these events is difficult given the rare nature of events that truly require immediate intervention. In particular, the rare nature of emergency events may result in machine learning models that are trained to detect emergency events without enough "positive" examples in associated training data (i.e., examples of emergency events) to be able to accurately identify emergency events.

One solution to this problem is to utilize differential diagnosis techniques to process information received regarding events. In particular, in response to receiving an identifier about an event (e.g., a computer security event, a medical event, and the like), a computer system may sequentially process a set of inquiries. In particular, the set of inquiries may be traversed by selecting future inquiries for processing based on responses to one or more previous inquiries. Processing individual inquiries may include answering one or more questions (e.g., automatically using associated computing processes and/or manually based on responses received from users). As the set of inquiries are processed, the computer system may store the responses in a tensor data structure, which may have data fields (e.g., rows) for each of the inquiries within the set of inquiries. Once a sufficient number of individual inquiries have been processed, the tensor data may be provided to a machine learning model, which may classify the event based on the responses indicated within the tensor. In certain instances, the machine learning model may classify the event as an emergency event requiring immediate intervention. Accordingly, the computer system may generate an intervention, which may include one or more of an alert, diagnosis, and/or recommended actions. In certain implementations, the computer system may automatically execute one or more of the recommended actions.

FIG. 1 illustrates a system 100 for differential diagnosis feature engineering according to an exemplary embodiment of the present disclosure. The system 100 includes computer systems 102, 104 and a network 106. The computer system 102 may be configured to receive and process event identifiers 112 corresponding to particular events 110 and may determine whether the events 110 indicate that an emergency event has occurred, requiring immediate intervention. In particular, the computer system 102 may be configured to determine a classification 146 for received events 110 and to determine, based on the classification 146, an intervention 120 for the event 110. The events 110 may include any type of occurrence capable of generating an alert or data. For example, the events 110 may include a computer security event indicative of a potential security breach, or the risk of a potential security breach (e.g., in the computer system 102 or in another computer system). As another example, the events 110 may include a medical event indicative of a potential medical emergency (e.g., a medical diagnosis requiring immediate or quick intervention by a medical professional).

The computer system 102 may receive event identifiers 112 from a monitoring system. For example, event identifiers 112 may be received for computer system security events that correspond to a potential breach in security for a computer system (e.g., the computer system 102 or another computer system, such as a computer system connected to the network 106). In such instances, event identifiers 112 may be received from a Security Information and Event Management (SIEM) system, such as Azure Monitor, Splunk Enterprise Security, IBM QRadar, and ArcSight SIEM systems. As another example, event identifiers 112 may be received for potential medical events. In such instances, event identifiers 112 may be received from a medical database or medical monitoring system. The event identifier 112 may contain event data 122, which may differ depending on the type of event 110 corresponding to the event identifier 112. For example, the event data 122 may contain one or more of network access information, a packet received from another computer system by the network 106, a medical scan, and/or patient information, depending on the type of event 110.

Upon receiving the event identifier 112, the computer system 102 may be configured to process a set of inquiries 114. The inquiries 114 may contain a plurality of inquiries 124, 126, 128, 130, 132, 134, 136. Each inquiry 124, 126, 128, 130, 132, 134, 136 may include a question regarding the contents of the event identifier 112 (e.g., the event data 122) and/or other data (e.g., contextual data regarding the event 110).

The computer system 102 may also generate a tensor 116 based on the inquiries 114. In particular, the computer system 102 may generate a response 138, 140, 142, 144 for the subset of inquiries 124, 128, 134, 136 processed in response to the event identifier 112. These responses 138, 140, 142, 144 may be added to the tensor 116. The tensor 116 may be implemented as an N-dimensional array of data (e.g., where N is greater than or equal to 1). As used throughout the present disclosure, the term "tensor" may refer to a tensor data structure (e.g., an N-dimensional array of data) and/or to data contained within a tensor data structure (e.g., responses 138, 140, 142, 144 and/or NULL indicators). Furthermore, one skilled in the art may understand that data contained within tensors 116 as discussed in the present disclosure may be stored in one or more alternative data structures (e.g., vectors, flat files, or other data analysis formats). All such implementations are considered within the scope of the present disclosure.

The tensor 116 may contain a corresponding field for each of the individual inquiries 124, 126, 128, 130, 132, 134 contained within the set of inquiries 114. In certain implementations, the tensor 116 may contain (i) a field identifying a corresponding inquiry 124, 126, 128, 130, 132, 134 and/or (ii) a field containing the response 138, 140, 142, 144 for corresponding processed inquiries. In such implementations, the tensor 116 may be implemented as a ragged tensors containing multiple nested, variable-length lists, wherein each list contains responses to inquiries in different categories (e.g., concerning different types of events). Inquiries 126, 130, 132 that have not been processed by the computer system 102 in response to the event identifier 112 may contain a NULL, Boolean false, integer zero, or other default data value to indicate that these inquiries 126, 130, 132 have not been processed for the event identifier 112. By contrast, inquiries 124, 128, 134, 136 processed in response to the event identifier 112 may contain corresponding responses 138, 140, 142, 144 containing the results and/or answers for the corresponding inquiries 124, 128, 134, 136. The responses 138, 140, 142, 144 may vary in format according to the type of inquiry 124, 128, 134, 136. For example, the inquiry 124 may be a true/false question, and the response 138 may contain a Boolean true or false value. As another example, the inquiry 128 may contain a range of acceptable values (e.g., a predefined range of acceptable integers), and the response 140 may contain one of the acceptable values (e.g., and integer within the predefined range). One skilled in the art will appreciate that, in additional or alternative implementations, the responses 138, 140, 142, 144 may contain data of other value types (e.g., strings, enumerated values, floating-point numbers, and the like. In certain implementations, the computer system 102 may be configured to only process a subset of the set of inquiries 114. For example, the inquiries 124, 128, 134, 136 may be processed by the computer system 102 in response to the event identifier 112. Accordingly, these inquiries 124, 128, 134, 136 have corresponding responses 138, 140, 142, 144 within the tensor 116. The subset of inquiries 124, 128, 134, 136 processed in response to the event identifier 112 may be selected based on the responses to individual inquiries. In particular, a subset of the inquiries 114 may be processed as an ordered set, and responses to one or more previous inquiries may determine which additional inquiries are subsequently processed. For example, the response 138 to the inquiry 124 may be used to select the inquiry 128 for processing. As another example, the responses 138, 140, and 142 to the inquiries 124, 128, 134 may be used to select the inquiry 136 for processing. In certain implementations, the computer system 102 may store mappings between individual inquiries 124, 126, 128, 130, 132, 134, 136 based on potential responses received. A mapping may include an association between values for one or more responses (e.g., valid response values) to particular inquiries 124, 126, 128, 130, 132, 134, 136 and one or more subsequent inquiries 124, 126, 128, 130, 132, 134, 136 for future processing.

Figure 2A:
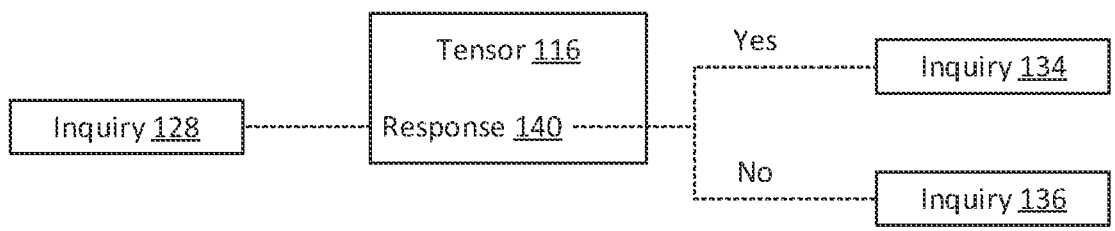
FIGS. 2A-2B illustrate inquiry mappings according to an exemplary embodiment of the present disclosure.
Figure 2B:
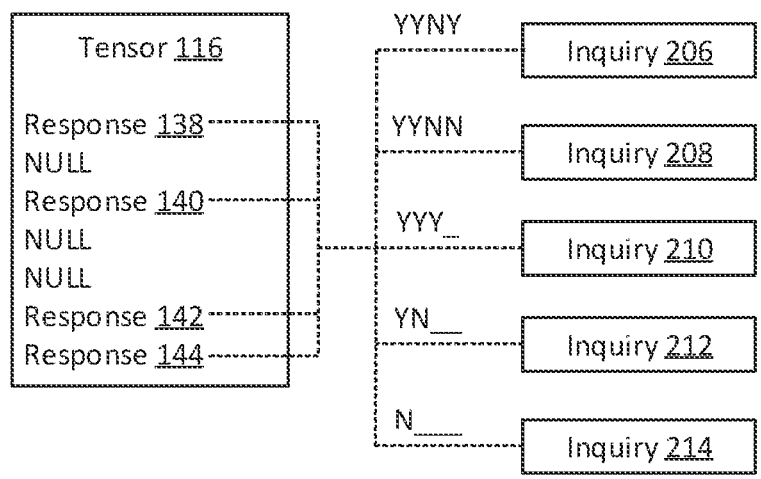

For example, FIGS. 2A-2B illustrate inquiry mappings 200, 202 according to an exemplary embodiment of the present disclosure. The mapping 200 selects between subsequent inquiries 134, 136 based on the response 140 received to the inquiry 128. In particular, the inquiry 128 may have two valid responses: yes, no (e.g., Boolean true, Boolean false). The mapping 200 specifies that, when the response 140 is yes (e.g., or Boolean true), the next inquiry that is processed is the inquiry 134. The mapping 200 also specifies that, when the response 140 is no (e.g., or Boolean false), the next inquiry that is processed is the inquiry 136. In additional or alternative implementations, the inquiry 128 may contain other types of acceptable responses (e.g., a range of numerical values, strings). In such instances, the mapping 200 may specify a corresponding inquiry for each of the valid acceptable responses (e.g., a corresponding inquiry for each acceptable numerical value, for ranges of acceptable numerical values, for strings with particular contents, for strings lacking particular contents).

The mapping 202 demonstrates how a subsequent inquiry may be selected based on the responses to multiple previous inquiries. In particular, the mapping 202 selects between inquiries 206, 208, 210, 212, 214 based on the responses 138, 140, 142, 144 to inquiries 124, 128, 134, 136. In particular, the mapping 202 specifies a corresponding inquiry 206, 208, 210, 212, 214 for each possible combination of responses 138, 140, 142, 144. In the depicted example, each of the responses 138, 140, 142, 144 are selected between yes and no (e.g., Boolean true, Boolean false) based on the inquiries 124, 128, 134, 136. In particular, if the responses 138, 140, 144 are yes and the response 142 is no, the mapping 202 indicates that the next inquiry selected should be the inquiry 206, which the computer system 102 may then proceed with processing (e.g., after processing the response 144). Similarly, if the responses 138, 140 are yes and the responses 142, 144 are no, the computer system 102 may proceed with processing the inquiry 208 according to the mapping 202. Further, if the responses 138, 140, 142 are yes, the computer system 102 may proceed with processing the inquiry 210, regardless of the value for the response 144. Similarly, if the response 138 is yes and the response 140 is no, the computer system 102 may proceed with processing the inquiry 212, regardless of the responses 142, 144. Additionally, if the response 138 is no, the computer system 102 may proceed with processing the inquiry 214, regardless of the responses 140, 142, 144.

The computer system 102 may thus be able to select subsequent inquiries from among the set of inquiries 114 based on the values for the responses 138, 140, 142, 144. While processing the set of inquiries 114, the computer system 102 may determine responses 138, 140, 142, 144 to one inquiry 124, 128, 134, 136 at a time. In additional or alternative implementations, the computer system 102 may determine multiple responses 138, 140, 142, 144 to multiple inquiries 124, 128, 134, 136 at the same time. For example, where selecting a subsequent inquiry 206, 208, 210, 212, 214 depends on responses 138, 140, 142, 144 to multiple inquiries 124, 128, 134, 136, the computer system 102 may determine the responses 138, 140, 142, 144 at least partially in parallel.

In certain instances, responses 138, 140, 142, 144 may be received from a user. For example, the computer system 102 may present the inquiry 124, 128, 134, 136 to a user (e.g., a medical professional, a computer security analyst) via a graphical user interface (e.g., executing on the computer system 102 and/or another computer system, such as a computer system associated with the user). In such instances, the user may enter the response 138, 140, 142, 144 via the graphical user interface, and the computer system 102 may receive the response 138, 140, 142, 144 (e.g., directly via a graphical user interface executing on the computer system 102 and/or via the network 106).

In additional or alternative implementations, certain responses 138, 140, 142, 144 may be determined on an automated basis. For example, the computer system 102 and/or another computer system 104 may determine the response 138, 140, 142, 144 using a computing process 108 associated with the inquiry 124, 128, 134, 136. For example, the set of inquiries 114 may identify corresponding computing processes 108 for individual inquiries 124, 126, 128, 130, 132, 134, 136. The computer system 102 may retrieve the corresponding computing process and/or may cause another computer system 104 to retrieve the computing process 108 and may execute the computing process 108 to determine a corresponding response 138, 140, 142, 144. In one specific example, where the event identifier 112 corresponds to the computer security event 110, the computing process 108 may execute to pull network traffic associated with the computer system 104 (e.g., a computer system suspected of breaching a security protocol) and to analyze the network traffic for a particular indicator of a security breach (e.g., a change in geographic location for a user of the computer system 104). As another example, where the event identifier 112 corresponds to a medical event 110, the computing system 108 may execute (e.g., on the computer system 102 and/or on the computer system 104) to analyze event data 122 (e.g., a medical scan) to determine whether the event data includes a particular risk indicator for an associated patient (e.g., a potential tumor or infection). In practice, the computing process 108 may be implemented according to one or more predefined heuristics and/or machine learning models. For example, the computing process 108 may include a heuristic configured to analyze particular types of network traffic. As another example, the computing process 108 may include a machine learning model trained to identify potential tumors within medical scans.

Although the inquiries 114 as depicted only include seven individual inquiries 124, 126, 128, 130, 132, 134, 136, in practice, the set of inquiries 114 may include hundreds or thousands of individual inquiries. Accordingly, conventional human techniques of responding to received event identifiers 110 may typically be unable to sequentially process the set of inquiries (i.e., because humans are not capable of accurately remembering mappings between such large numbers of inquiries). The set of inquiries 114 may be at least partially generated based on feedback from users or other individuals. For example, the set of inquiries 114 may be generated based on an ordered list of indicators that a user (e.g., a computer security analyst, a medical professional) may consult when determining whether a particular event (e.g., a computer security event, a medical event) requires immediate intervention. As one example, the set of inquiries 114 utilized in response to computer security events may be generated by aggregating analysis techniques for multiple types of computer security events (e.g., for DDoS attacks, for stolen user credentials, and the like). As another example, the set of inquiries 114 utilized in response to received medical events may be generated based off medical diagnosis protocols, such as the Diagnostic and Statistical Manual of Mental Disorders (DSM). In additional or alternative implementations, the set of inquiries may be at least partially generated by a machine learning model. For example, as discussed further below, a machine learning model (such as the machine learning model 118) may be trained to analyze tensors 116 and to determine which responses 138, 140, 142, 144 are most closely related to different types of classifications. In such implementations, the machine learning model 118 may be further trained to generate mappings between inquiries 124, 128, 134, 136 that are associated with the same types of diagnoses. For example, the machine learning model 118 may determine that the responses 140, 142, 144 are relevant to detecting DDoS attacks. In such instances, the machine learning model 118 may generate a mapping that links the inquiries 128, 134, 136 such that a response 140 (e.g., a Boolean true response) to the inquiry 128 causes the inquiry 134 to be selected and a response 142 (e.g., a Boolean false response) to the inquiry 134 causes the inquiry 136 to be selected. Furthermore, in practice, the same set of inquiries 114 may be used in response to each received event identifier 112. For example, the same set of inquiries 114 may be used in response to every event identifier 112 associated with computer security events. As another example, the same set of inquiries 114 may be used in response to every event identifier 112 associated with medical events.

The computer system 102 may continue to process individual inquiries 124, 126, 128, 130, 132, 134, 136 until reaching a stopping condition. The stopping condition may include one or more of (i) a predetermined number of questions is reached, (ii) a predetermined amount of time has passed, and/or (iii) no further corresponding inquiries remain within mappings for the set of inquiries 114.

The computer system 102 may then provide the tensor 116 to a machine learning model 118. The machine learning model 118 may be configured to analyze the responses 138, 140, 142, 144 within the tensor 116 to determine a classification 146 for the event identifier 112. For example, the machine learning model 118 may be a classifier model, such as a decision tree, a neural network, a random forest, a support vector machine, a nearest neighbor model, and the like. In certain implementations, the machine learning model 118 may include more than one machine learning model. In particular, the machine learning model 118 may be configured to classify received tensors between one of a plurality of different classifications 146. For example, where the event 110 is a computer security event, the classifications 146 may include different types of security breaches or incursions. As another example, where the event 110 is a medical event, the classifications 146 may include different types of diagnoses for medical emergencies. The machine learning model 118 may be configured to determine a closest corresponding classification 146 based on the tensor 116. In certain instances, the machine learning model 118 may determine that there is no corresponding classification 146 for a tensor 116. For example, the machine learning model 118 may determine, based on the tensor 116, that the event 110 corresponding to the event identifier 112 does not require immediate intervention, and may therefore identify no classification for the event identifier 112 based on the tensor 116.

The machine learning model 118 may be trained by providing the machine learning model 118 with predetermined tensors that correspond to known classifications. However, in practice, examples of events 110 (e.g., computer security events) requiring immediate intervention may be rare, resulting in a class imbalance for real-world example tensors. Accordingly, training the machine learning model 118 with a representative sample of tensors may cause the machine learning model 118 to incorrectly identify too many received tensors as not requiring immediate intervention. To correct this class imbalance, it may be necessary to generate or isolate additional training examples of events that require immediate intervention. For example, training tensors may be generated based on published examples (e.g., of security incursions, emergency medical events), a manual audit of classifications by the machine learning model 118 (e.g., to identify tensors 116 that were incorrectly classified), and/or may be created based on examples from subject matter experts (e.g., security analysts, medical analysts). These training examples may be added to a database, which may be used to train the machine learning model 118 on an ongoing basis (e.g. at regular intervals such as every hour, every day, every week, every month, every year).

Based on the classification 146, the computer system 102 may generate an intervention 120. The intervention 120 may include one or more files containing recommended or required actions for addressing or reducing the risk presented by the event 110. For example, the intervention 120 may include one or more of an alert 148, diagnosis 150, and an action 152. The alert 148 may include a notice to an associated user or computing process in order to take immediate action regarding the events 110 (e.g., to further analyze the event, to prevent computer security intrusion, to perform a medical intervention). The diagnosis 150 may include an indication of the type of problem indicated by the events 110 (e.g., computer security risk, medical problem requiring intervention). In certain implementations, the diagnosis 150 may include the classification 146 generated by the machine learning model 118. The action 152 may include a recommended next action in order to further process or halt the events 110. The action 152 may, in certain implementations, be automatically performed by the computer system 102 or another computer system. For example, the action 152 may include taking steps to verify a user access attempt that presents a computer security risk (e.g., presenting a two factor authentication challenge, restricting network access for suspected compromised credentials, restricting network access to a suspected computer device). As another example, the action 152 may include further diagnostic action for a medical event (e.g., scheduling medical appointments, allocating medical resources). Such automated execution of events may enable immediate or real-time responses to events 110 (e.g., computer security events, medical events), which may not be possible when users are required to manually analyze received event identifiers.

The computer systems 102, 104 include processors 156, 158 and memories 160, 162. The processors 156, 158 and memories 160, 162 may implement one or more aspects of the computer systems 102, 104. For example, the memories 160, 162 may store instructions which, when executed by the processors 156, 158, may cause the processors 156, 158 to perform one or more operational features of the computer systems 102, 104. Additionally, the computer systems 102, 104 may be configured to communicate with one another (and/or other computer systems) using the network 106. For example, the computer systems 102, 104 may communicate with the network 106 using one or more wired network interfaces (e.g., Ethernet interfaces) and/or wireless network interfaces (e.g., Wi-Fi®, Bluetooth®, and/or cellular data interfaces). In certain instances, the network 106 may be implemented as a local network (e.g., a local area network), a virtual private network, L1 and/or a global network (e.g., the Internet).

Figure 3:
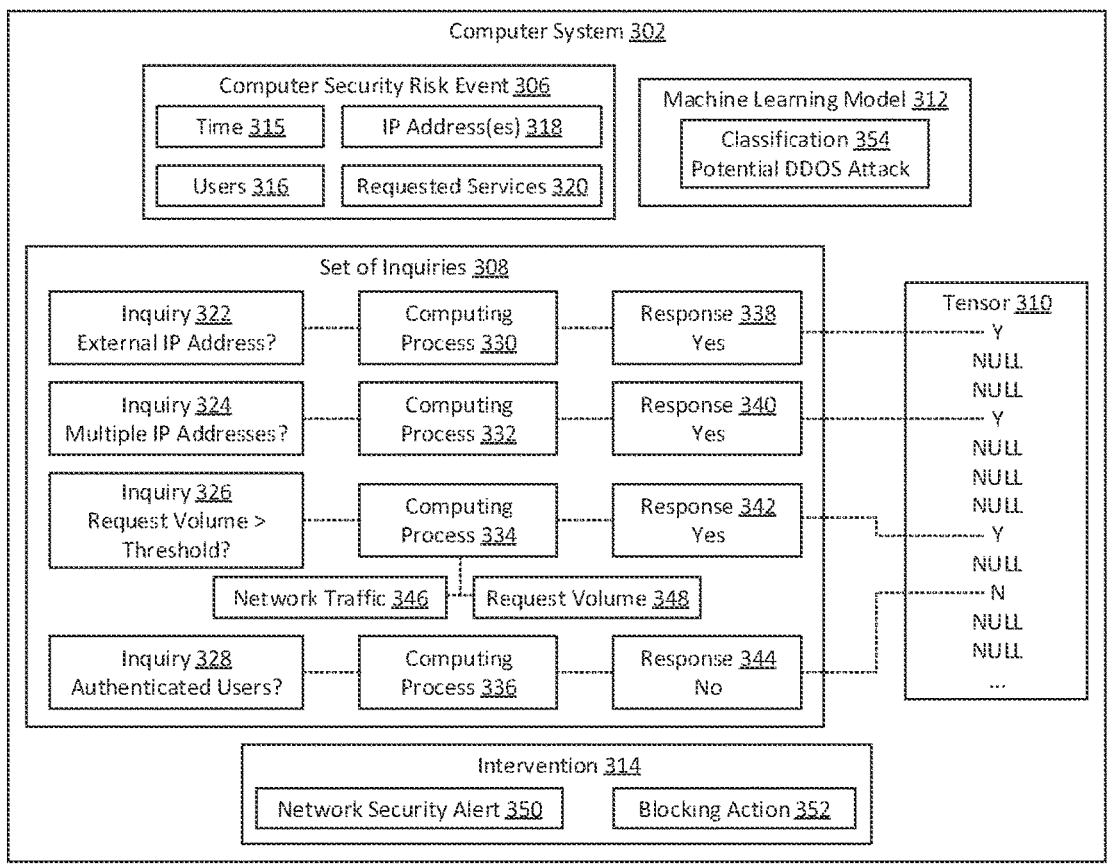
FIG. 3 illustrates a system for differential diagnosis feature engineering of a received computer security event according to an exemplary embodiment of the present disclosure.

FIG. 3 illustrates a system 300 for differential diagnosis feature engineering of received computer security events according to an exemplary embodiment of the present disclosure. The system 300 includes a computer system 302, which may be an exemplary implementation of the computer system 102. In particular, the computer system 302 may be an exemplary implementation of the computer system 102, configured to receive alerts or other event identifiers regarding computer security events 306.

Computer security events 306 may include a breach or other compromise of one or more secured computer systems, computing resources, software services, data stored within a computer system, or any other compromise of security protocols for a computer system. The computer security events 306 may concern a breach in security for the computer system 302 and/or a breach in security for another computer system (e.g., computer system on the same network as the computer system 302, a computer system in a cloud computing environment containing or associated with the computer system 302, and the like).

The computer system 302 may receive the computer security event 306 via a network. In particular, the computer security event 306 may be an exemplary implementation of the event identifier 112 received by the computer system 102. The computer security event 306 includes a time 315, users 316, IP addresses 318, and requested services 320. The time 315 may include a time at which the security event occurred in the users 316 may identify the one or more user credentials that were used in connection with the computer security event 306. For example, the computer security events 306 may include a DDoS attack on a computing service associated with the computer system 302. The time 315 may include a time (or time range) for the suspected DDoS attack, and the users 316 may include user information provided in connection with access requests as part of a suspected DDoS attack. The IP addresses 318 may specify IP addresses from which the suspected DDoS attack received requests, and the requested services 320 may identify the computing services identified by the requests associated with the computer security events 306.

In response, the computer system 302 may process a set of inquiries 308, which may be an exemplary implementation of the set of inquiries 114. In particular, the computer system 302 may initially process the inquiry 322, which asks whether external IP addresses were involved with the computer security event 306. The inquiry 322 has a corresponding computing process 330, which may be stored within the set of inquiries 308 as depicted and/or may be stored within a database or other data store communicatively coupled to the computer system 302. The computing process 30 may be previously configured to analyze IP addresses 318 contained within the computer security event and to determine whether any of the IP addresses 308 or associated with external computing devices (e.g., external to a local network of the computer system 302 and associated computing services. After executing the computing process 330, the computing system 302 may determine a response 338 to the inquiry 322, indicating that external IP addresses were present within the computer security event 306 (e.g., a "yes" and/or Boolean true value). Based on the response 338, the computer system 302 may select the inquiry 324 from the set of inquiries 308. In particular, a mapping (not depicted) may identify the inquiry 324 the response 338 to the inquiry 322 is "yes."

The inquiry 324 asks whether there are multiple IP addresses present within the computer security event 306. The computer system 302 may execute corresponding computing process 332 in order to generate a response 340 to the increased 324. In particular, the system 302 executes the computing process 332 to analyze the IP addresses 318 included within the computer security event 306 and determine whether there are multiple IP addresses present within the computer security event 306. As depicted, the computer system 302 may determine that there are multiple IP addresses present within the IP addresses 318 contained within the computer security event 306. Based on the response 340 (e.g., and a corresponding mapping for the set of inquiries 308), the computer system 302 may then identify the inquiry 326 as the next inquiry to be processed. The inquiry 326 asks whether the requested volume is greater than a predetermined threshold. Request volume is not contained within the computer security event 306. Accordingly, while executing the corresponding computing process 334, the computer system 302 may access external data, such as copies of network traffic 346. For example, the computer system 302 may request a copy of a log file from a Security Information and Event Management (SIEM) system. The computer system, according to the computing process 334, may parse the network traffic 346 to identify requests for the requested services 320. Based on the identified requests, the computing process 334 may cause the computer system 302 to calculate a request volume 348 for the requested services 320. The computer system 302 may then compare the request volume 348 to a predetermined threshold and determine that the request volume 348 exceeds the predetermined threshold. For example, the request volume 348 may indicate that the requested services 320 are receiving 100,000 requests per hour, and the predetermined threshold may be 75,000 requests per hour. Accordingly, the response 342 indicates a "yes" or Boolean true, and the computer system 302 may identify the inquiry 328 as the next inquiry to process (e.g., according to a mapping for the set of inquiries 308).

The inquiry 328 asks whether the users issuing the requests are authenticated (e.g., users 316 that have provided authenticated credentials, users 316 that have passed a two factor authentication challenge). For example, the inquiry 328 may ask whether all of the users issuing requests are authenticated, or if at least a predetermined threshold of the users are authenticated. The computer system 302 may determine that a sufficient proportion of the users 316 are not authenticated users, and may store this determination in the response 344.

While processing the inquiries 322, 324, 326, 328, the computer system 302 may add corresponding entries to the tensor 310 in fields corresponding to the responses 338, 340, 342, 344. Data fields within the tensor 310 for inquiries that were not processed from the set of inquiries 308 may include a null indicator. The computer system 302 may then provide the tensor 310 to a machine learning model 312, which may be configured to classify tensors 310 into one of a plurality of potential computer security incursions. For example, the machine learning model 312 may determine a classification 354 for the computer security event 306 based on the tensor 310 as a potential DDoS attack. In particular, the presence of multiple external addresses and request volumes from unauthenticated users in large quantities may indicate a potential DDoS attack requiring immediate action.

In response the classification 354, the computer system 302 may generate an intervention 314. The intervention 314 may include a network security alert 350 and/or a blocking action 352 for example, the network security alert 350 may be generated to indicate that a potential DDOS attack is in progress for the requested services 320. The network security alert 350 may identify other information regarding the potential DDOS attack (e.g., origin locations for the IP addresses 318, request volume 348). The network security alert 350 may be presented to the computer security analyst (e.g., via a SIEM system). The blocking action 352 may be generated to interrupt or prevent additional requests from denying service. For example, blocking action 352 may include one or more of requiring user authentication for the requested services 320, restricting bandwidth for the requested services 320, blocking IP addresses 318 associated with unauthenticated users, and the like. In certain implementations, the blocking action 352 may be automatically implemented by the computer system 302. In additional or alternative implementations, the blocking action 352 may require user approval before being implemented. For example, the blocking action 352 may be included as a recommended action within the network security alert 350.

In this way, the computer system 302 may be able to receive and process computer security events. In particular, the set of inquiries 308 may enable the computer system 302 to differentiate (e.g., using differential diagnosis questioning as described above) between different types of computer security breaches. For example, although the depicted example focuses on DDoS attacks, the computer system 302 may operate similarly to detect, privilege escalation, lateral movement, data exfiltration, and any other type of breach of computer security. Furthermore, generating a classification for received computer security events may allow the computer system 302 to automatically take action (e.g., a blocking action), preventing further security compromises as a result of any suspected security breaches much faster than if computer security events were manually reviewed by an analyst.

Figure 4:
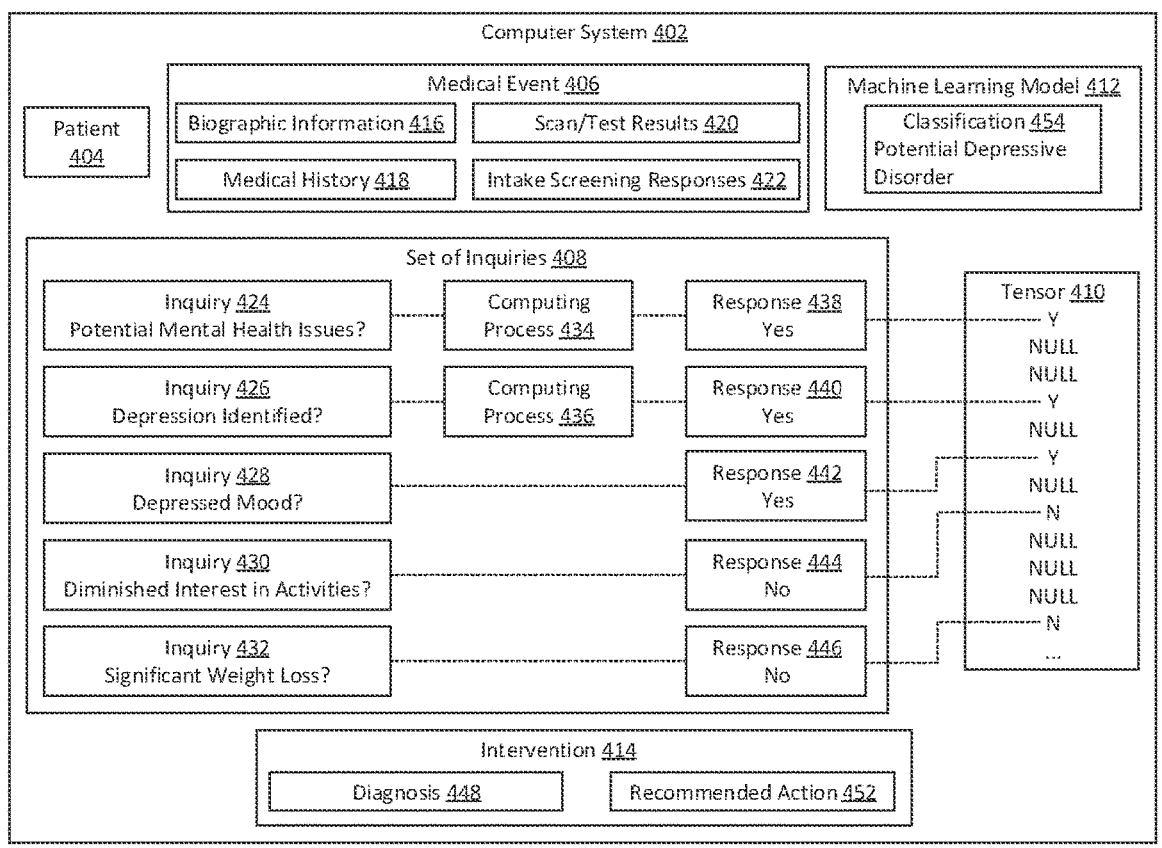
FIG. 4 illustrates a system for differential diagnosis feature engineering of a received medical event according to an exemplary embodiment of the present disclosure.

FIG. 4 illustrates a system 400 for differential diagnosis feature engineering of a received medical event according to an exemplary embodiment of the present disclosure. The system 400 includes a computer system 402, which may be an exemplary implementation of the computer system 102. In particular, the computer system 402 may be an exemplary implementation of the computer system 102, configured to receive alerts or other event identifiers regarding medical events 406.

Medical events 406 may include medical treatments or diagnostic events, such as medical scans, visits to a doctor, discussions with a medical professional (e.g., a doctor, a nurse, a surgeon, a pharmacist, and the like). The medical events may concern individual patients, such as the patient 404. In certain implementations, the computer system 402 may be configured to analyze received medical events 406 to determine whether immediate medical intervention is needed and/or to determine a potential medical diagnosis for the patient 404.

The computer system 402 may receive the medical event 406 via a network. In particular, the medical event 406 may be an exemplary implementation of the event identifier 112 received by the computer system 102. The medical event 406 may be received in response to the completion or partial completion of a medical process on behalf of the patient 404. Medical processes may include one or more medical appointments (e.g., routine medical screenings, physician consultations), hospital or doctor check-ins, diagnostic actions (e.g., medical scans, discussions with medical specialists), therapeutic actions (e.g., physical therapy, surgery), and the like. The medical event 406 includes biographic information 416, medical history 418, test results 420, and intake screening responses 422. The biographic information 416 may include biographic identifiers of the patient 404 (e.g., name, age, address, gender). The biographic information 416 may be received from the patient 404 (e.g., while checking into a doctor's office or hospital) and/or may be stored in association with an identifier of the patient 404 (e.g., based on information received during a previous visit by the patient 404). The medical history 418 may include previous medical conditions, therapeutic actions, diagnostic actions, and the like for the patient 404. Similar to the biographic information 416, the medical history 418 may be received from the patient 404 and/or may be stored in association with an identifier of the patient 404. The test results 420 may include results from recent medical tests performed on the patient 404 (e.g., blood tests, medical scans) and may be received from an imaging system and/or testing system that completed the medical tests. The intake screening responses 422 may include information received from a patient during an intake procedure (e.g., intake at a hospital and/or at a doctor's office).

The computer system 402 may process a set of inquiries 408 based on the medical event 406. In particular, the computer system 402 may initially process the inquiry 424, which asks whether the patient presents with any potential mental health issues. The inquiry 424 has an associated computing process 434, which may analyze the biographic information 416, medical history 418, and/or intake screening responses 422 in order to determine whether the patient 404 is presenting potential mental health issues. For example, the computing process 434 may be configured to analyze the intake screening responses 422 received from the patient 404 to determine whether the patient 404 is seeking help for mental health issues (e.g., based on keywords identifying particular mental health ailments). The patient 404 may have come into a doctor's office and may have indicated during intake screening that their moods have been lower than usual recently. This information may be reflected in the intake screening responses 422, and the computing process 434 may accordingly determine that potential mental health issues have been detected, generating a response 438 containing a yes value and/or a Boolean true value. Based on this response 438, the computer system 402 may identify the inquiry 426 as the next inquiry for processing.

The inquiry 426 asks whether depression is identified as one of the potential mental health issues for the patient 404. Computing process 436 associated with the inquiry 426 analyzes information contained within the medical event 406 (e.g., medical history 418, intake screening responses 422) to determine whether depression screening is necessary for the patient 404. For example, the computing process 436 analyzes the medical history 418 to determine whether the patient 404 has a history of depression or other mental health issues. Additionally or alternatively, the computing process 436 may cause the computer system 402 to analyze the intake screening responses 422 for potential mentions of depression and/or depression symptoms. For example, the patient 404 may have a history of depression and, based on the intake screening responses 422 indicating a lower mood for the patient 404, the computing process 436 may determine that depression screening is necessary, as reflected in the response 440. Based on the response 440, the computer system 402 may determine that the inquiries 428, 430, 432 are the next inquiries to be processed. In particular, the inquiries 428, 430, 432 may be selected based on the DSM-V diagnosis requirements for depressive disorders, reflected by a mapping between the response 440 (e.g., a yes response 440) and the inquiries 428, 430, 432. The inquiries 428, 430, 432 may be presented to a user (e.g., the patient 404, a doctor, a nurse) via a graphical user interface. The user may enter responses 442, 444, 446 by the graphical user interface, the computer system 402 may receive these responses 442, 444, 446.

While processing the inquiries 424, 426, 428, 430, 432, the computer system 402 may add corresponding entries to the tensor 410 in fields corresponding to the responses 438, 440, 442, 444, 446. Data fields within the tensor 410 for inquiries that were not processed from the set of inquiries 308 may include a null indicator. The computer system 402 may then provide the tensor 410 to a machine learning model 412, which may be configured to classify tensors 410 into one of a plurality of potential diagnoses. For example, the machine learning model 402 may determine, based on the tensor 410, a classification 454 for the medical event 406 and the patient 404 indicating a potential depressive disorder for the patient 404.

In response to the classification 454, the computer system 402 may generate an intervention 414. The intervention 414 may include a diagnosis 448 and a recommended action 452. The diagnosis 448 may represent a predictive diagnosis based on the classification 454. For example, the diagnosis 448 may include the classification 454 (e.g., that the patient 404 has a potential depressive disorder). The recommended action 452 may identify proposed next steps to take in treating the patient 404. For example, the recommended action 452 may indicate that the patient 404, or a medical professional on the patient's 404 behalf, should schedule an appointment with a psychiatrist or therapist. In certain implementations, the intervention 414 may be presented as an alert to the patient 404 and/or another medical professional. In additional or alternative implementations, the computer system 402 may automatically implement one or more recommended actions 452. For example, the computer system 402 may automatically schedule an appointment with a doctor or therapist on behalf of the patient 404 and/or may present to the patient 404 with the available appointment times for one or more identified doctors.

In this way, the computer system 402 may be able to receive and process medical events to determine when medical intervention may be necessary for patients. Although the discussed examples focus on mental health diagnoses for the patient 404, it should be understood that, in practice, the set of inquiries 408 may enable the computer system 402 to process inquiries regarding other types of medical issues. For example, the set of inquiries 408 may include individual inquiries regarding cancer, digestive issues, or other medical ailments. Furthermore, generating a classification for received medical events may allow the computer system 402 to automatically take action (e.g., scheduling an appointment, notifying or calling a specialist for follow-up review), decreasing response time and improving patient outcomes over techniques that require manual review of medical events.

Figure 5:
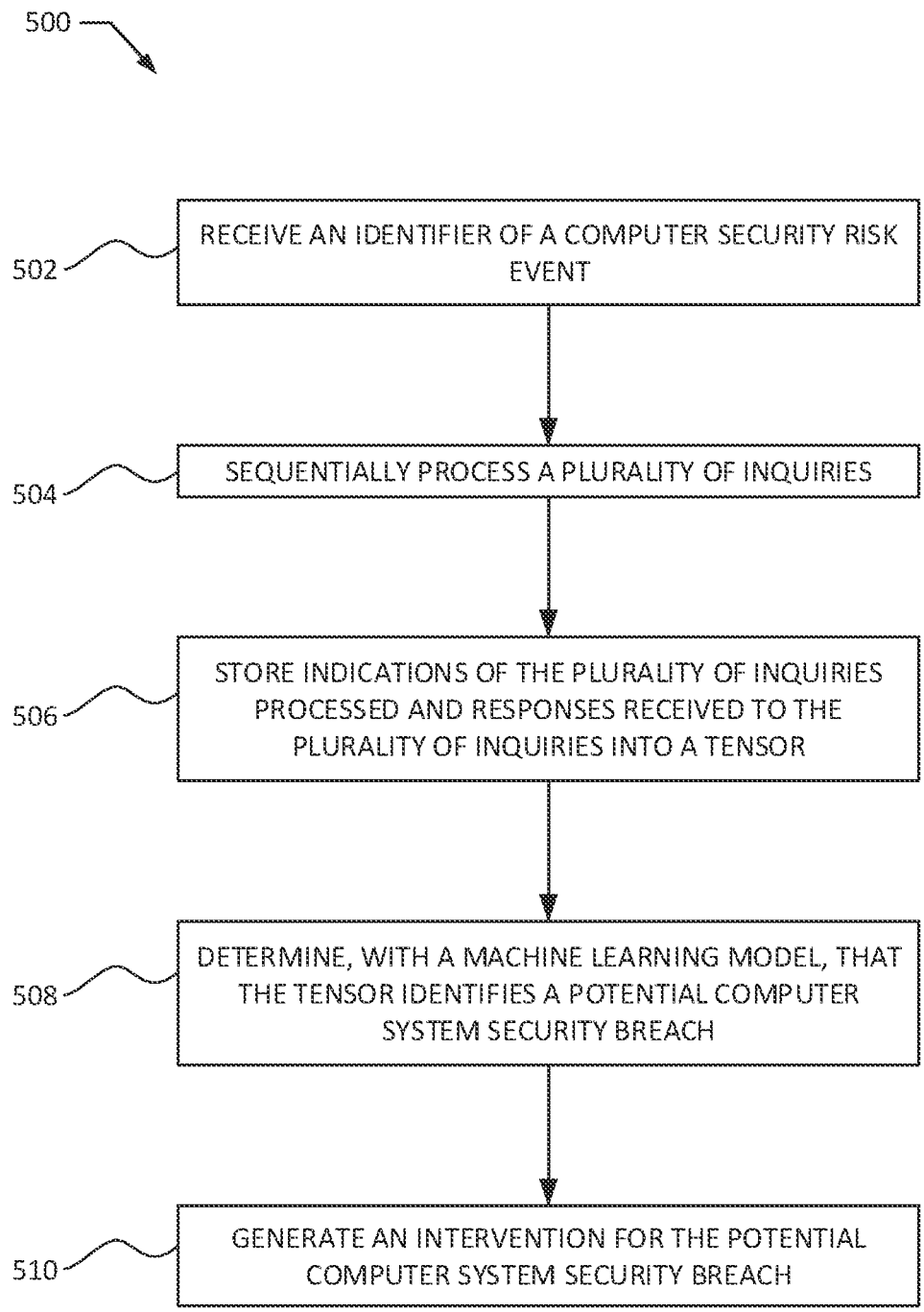
FIG. 5 illustrates a method for differential diagnosis feature engineering of a received computer security event according to an exemplary embodiment of the present disclosure.

FIG. 5 illustrates a method 500 for differential diagnosis feature engineering of received computer security event according to an exemplary embodiment of the present disclosure. The method 500 may be implemented on a computer system, such as the system 100, 300. For example, the method 500 may be implemented by the computer system 102 and/or the computer system 302. The method 500 may also be implemented by a set of instructions stored on a computer readable medium that, when executed by a processor, cause the computer system to perform the method 500. For example, all or part of the method 500 may be implemented by the processor 158 and the memory 162. Although the examples below are described with reference to the flowchart illustrated in FIG. 5, many other methods of performing the acts associated with FIG. 5 may be used. For example, the order of some of the blocks may be changed, certain blocks may be combined with other blocks, one or more of the blocks may be repeated, and some of the blocks described may be optional.

The method 500 may begin with receiving an identifier of a computer security event (block 502). For example, a computer system 102, 302 may receive an identifier 112 of a computer security event 110, 306. The identifier 112 may include event data 122 concerning the computer security event 110, 306, such as a time 315 for the event 110, 306, users 316 involved in the event 110, 306, IP addresses 318 involved in the event 110, 306, and/or requested services 320 associated with the event 110, 306. For example, the computer security event 110, 306 may include a request to access a computing service using compromised user credentials.

A plurality of inquiries may be sequentially processed (block 504). For example, the computer system 102, 302 may sequentially process a set of inquiries 308. In particular, the set of inquiries 114, 308 may be processed sequentially according to the responses received to individual inquiries. For example, the set of inquiries 114, 308 may include a mapping 200, 202 between responses and subsequent answers to be processed from the set of inquiries 114, 308. As explained further above, processing individual inquiries 124, 126, 128, 130, 132, 134, 136, 322, 324, 326, 328 may include executing an associated computing process 108, 330, 332, 334, 336 to retrieve additional information and/or to analyze associated data and determine the responses 138, 140, 142, 144, 338, 340, 342, 344. Additionally or alternatively, processing individual inquiries 124, 126, 128, 130, 132, 134, 136, 322, 324, 326, 328 may include receiving manual responses from a user (e.g., a computer security analyst).

Indications of the plurality of inquiries processed and responses received to the plurality of inquiries may be stored in a tensor (block 506). For example, indications of responses 138, 140, 142, 144, 338, 340, 342, 344 and the plurality of processed inquiries 124, 128, 134, 136, 322, 324, 326, 328 may be stored within a tensor 116, 310. For example, the tensor 116, 310 may include rows or corresponding data fields for each of the inquiries within the set of inquiries 114, 308. As responses 138, 140, 142, 144, 338, 340, 342, 344 are determined for processed inquiries 124, 128, 134, 136, 322, 324, 326, 328, the responses 138, 140, 142, 144, 338, 340, 342, 344 may be added to corresponding rows within the tensor 116, 310. For example, the computer system may process inquiries 124, 128, 134, 136, 322, 324, 326, 328 regarding compromised user credentials (e.g., request origin location, time since the user last authenticated) and may store the resulting responses in the tensor 116, 310.

A machine learning model may then be used to determine that the tensor identifies a potential computer security system breach (block 508). For example, a machine learning model 118, 312 may be used to determine that the tensor 116, 310 identifies a potential computer security breach. In particular, the machine learning model 118, 312 may be configured to generate a classification 146, 354 for the computer security event 306, 110 based on the tensor 116, 310 and the responses contained therein. For example, based on the tensor 116, 310, the machine learning model 118, 312 may determine that the computer security event 110, 306 represents potential use of compromised user credentials, which represents a potential computer security breach.

An intervention may be generated for the potential computer system security breach (block 510). For example, the computer system 102, 302 may generate an intervention 120, 114 for the potential computer security system breach represented by the computer security event 110, 306. In particular, the intervention 120, 314 may include one or more of generating a network security alert 350 for an associated user (e.g., a computer security analyst). Additionally or alternatively, the intervention 314 may include one or more automatic blocking actions 352 performed by the computer system 102, 302. For example, the computer system 102, 302 may present a two factor authentication challenge for a user suspected of utilizing compromised credentials and/or may block network traffic or refuse service requests for the user suspected of using compromised credentials.

Figure 6:
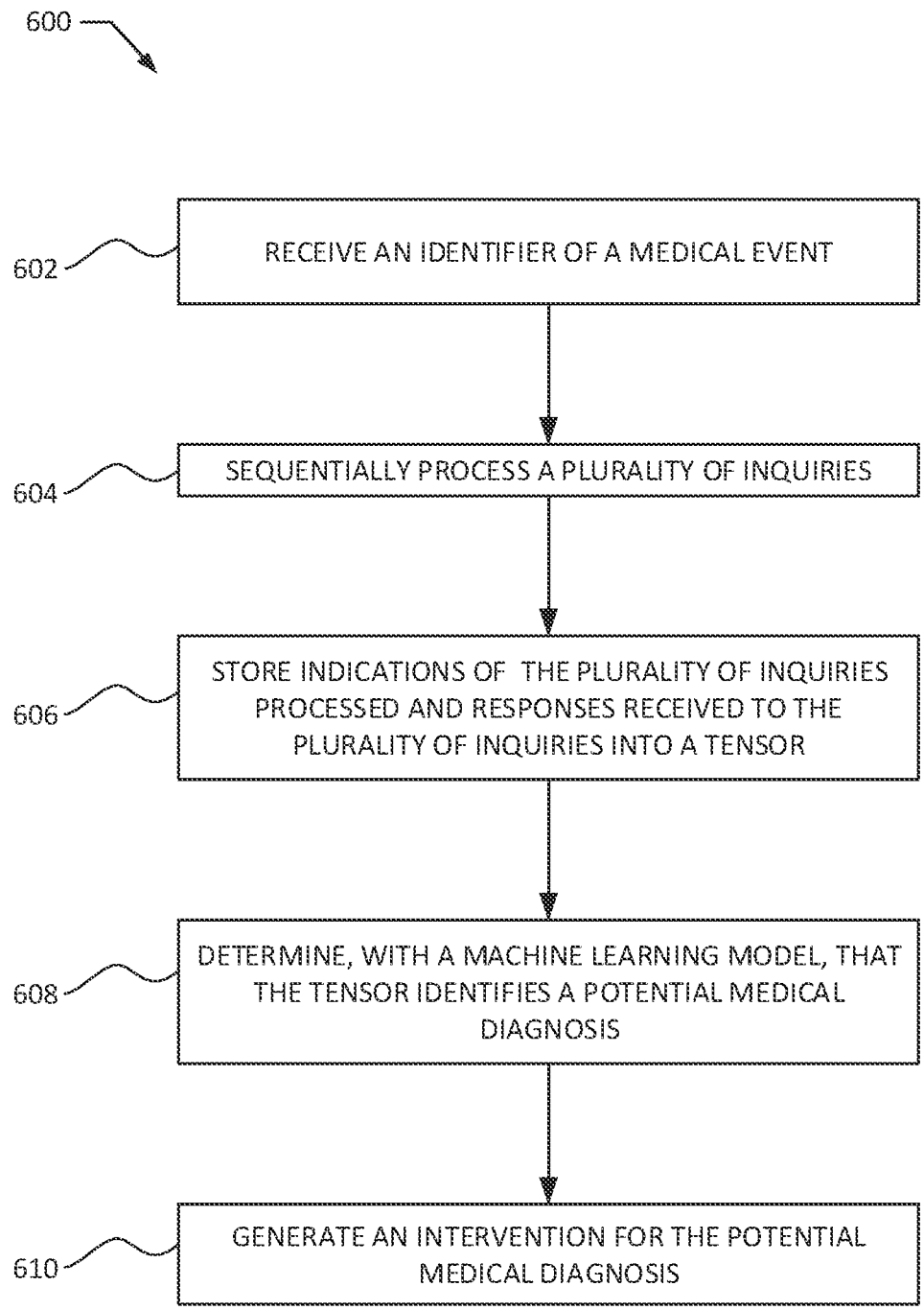
FIG. 6 illustrates a method for differential diagnosis feature engineering of a received medical event according to an exemplary embodiment of the present disclosure.

FIG. 6 illustrates a method 600 for differential diagnosis feature engineering of received health data according to an exemplary embodiment of the present disclosure. The method 600 may be implemented on a computer system, such as the system 100, 400. For example, the method 600 may be implemented by the computer system 102 and/or the computer system 402. The method 600 may also be implemented by a set of instructions stored on a computer readable medium that, when executed by a processor, cause the computer system to perform the method 600. For example, all or part of the method 600 may be implemented by the processor 158 and the memory 162. Although the examples below are described with reference to the flowchart illustrated in FIG. 6, many other methods of performing the acts associated with FIG. 6 may be used. For example, the order of some of the blocks may be changed, certain blocks may be combined with other blocks, one or more of the blocks may be repeated, and some of the blocks described may be optional.

The method 600 may begin with receiving an identifier of a medical event (block 602). For example, a computer system 102, 402 may receive an identifier 112 of a medical event 110, 406. The identifier 112 may be received in response to completing one or more medical tasks on behalf of a patient 404. For example, the patient may have recently received a chest x-ray, the completion of which may trigger the creation of the medical event 110, 406.

A plurality of inquiries may be sequentially processed (block 604). Indications of the plurality of inquiries and responses received to the plurality of inquiries may be stored in a tensor (block 606). These blocks may be implemented using techniques similar to those discussed above in connection with the system 400 and blocks 504, 506 of the method 500. In particular, the computer system 102, 402A sequentially process a set of inquiries 114, 408 relating to treatment of the patient 404. For example, processed inquiries may include questions regarding why the chest x-ray scan was performed (e.g., to detect potential lung infections, as determined based on the patient's 404 medical history 418) and whether the chest x-ray scan depicts medical issues requiring immediate intervention (e.g., whether the chest x-ray scan depicts a lung infection for the patient 404).

It may then be determined, with a machine learning model, that the tensor identifies a potential medical diagnosis (block 608). For example, the computer system 102, 302 may determine, with a machine learning model 118, 412, that the tensor 116, 410 identifies a potential medical diagnosis. In particular, the machine learning model 118, 412 may be configured to generate a classification 146, 454 for the medical event 406, 110 based on the tensor 116, 410 and the responses contained therein. For example, based on the tensor 116, 410, the machine learning model 118, 412 may determine that the medical event 110, 406 represents a potential lung infection, which may represent a potential medical diagnosis requiring medical intervention.

An intervention may be generated for the potential medical diagnosis (block 610). For example, the computer system 102, 402 may generate an intervention 120, 414 for the potential medical diagnosis represented by the medical event 110, 406. For example, the intervention 120, 414 may include a diagnosis 448 (e.g., a potential lung infection) and one or more recommended actions 452 (e.g., manual review of the chest x-ray by a trained analyst, scheduling an appointment with a medical professional, prescribing one or more antibiotics).

The methods 500, 600 thus enable computer systems to automatically detect and act to prevent or reduce damage by different types of emergency events, including computer security events, medical events, and any other type of event that may automatically generate data upon occurrence. Furthermore, the differential diagnosis enabled by the sequential processing of the inquiries may enable automatic processing of at least a portion of the responses necessary to determine whether a particular event is an emergency event. Accordingly, the methods 500, 600 reduce the time required to classify received events by automatically processing at least a portion of these responses. Furthermore, automated computer processes associated with the inquiries may be capable of answering questions a human cannot (e.g., parsing large network logs, aggregating medical data from multiple, disparate sources). Furthermore, when a generated intervention includes an action that is executed by the computer system, response time (e.g., for blocking computer system security breaches, for responding to immediate medical needs) may be dramatically improved over techniques that rely on manual review of events and event identifiers.

Figure 7:
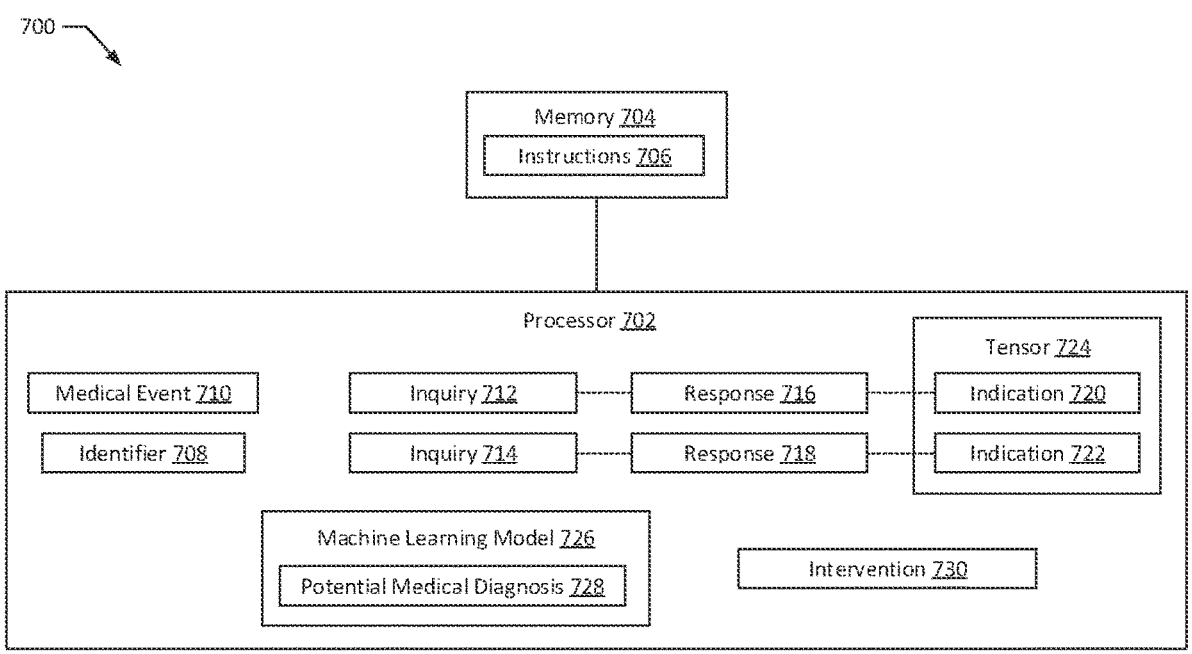
FIG. 7 illustrates a system according to an exemplary embodiment of the present disclosure.

FIG. 7 illustrates a system 700 according to an exemplary embodiment of the present disclosure. The system 700 includes a processor 702 and a memory 704. The memory 704 may store instructions 706 which, when executed by the processor 702, cause the processor 702 to receive an identifier 708 of a medical event 710 and sequentially process a plurality of inquiries 712, 714. Subsequent inquiries 712, 714 in the plurality of inquiries 712, 714 may be selected and asked based on responses 716, 718 to earlier inquiries 712, 714 in the plurality of inquiries 712, 714. The instructions 706 may also cause the processor 702 to store indications 720, 722 of (i) the plurality of inquiries 712, 714 processed and (ii) responses 716, 718 received to the plurality of inquiries 712, 714 into a tensor 724 and determine, with a machine learning model 726, that the tensor 724 identifies a potential medical diagnosis 728. The instructions 706 may further cause the processor 702 to generate an intervention 730 for the potential medical diagnosis 728.

Aspects of the subject matter described herein may be useful alone or in combination with one or more aspects described herein. In a first aspect, a method is provided that includes receiving an identifier of a computer system security event and sequentially processing a plurality of inquiries. Subsequent inquiries in the plurality of inquiries may be selected and asked based on responses to earlier inquiries in the plurality of inquiries. Indications of (i) the plurality of inquiries processed and (ii) responses received to the plurality of inquiries may be stored into a tensor and a machine learning model may be used to determine that the tensor identifies a potential computer system security breach. The method may also include generating an intervention for the potential computer system security breach.

In a second aspect according to any of the previous aspects (e.g., the first aspect), at least a first inquiry of the plurality of inquiries identifies subsequent inquiries based on the response received to the first inquiry.

In a third aspect according to any of the previous aspects (e.g., the first and second aspects), the inquiries are selected from a larger set of inquiries.

In a fourth aspect according to any of the previous aspects (e.g., the first through third aspects), the tensor has rows for each of the larger set of inquiries.

In a fifth aspect according to any of the previous aspects (e.g., the first through fourth aspects), the tensor contains null data values for rows corresponding to inquiries from the larger set of inquiries that are not contained in the plurality of inquiries.

In a sixth aspect according to any of the previous aspects (e.g., the first through fifth aspects), at least a subset of the plurality of inquiries are answered manually.

In a seventh aspect according to any of the previous aspects (e.g., the first through sixth aspects), at least a subset of the plurality of inquiries are answered automatically.

In an eighth aspect according to any of the previous aspects (e.g., the first through seventh aspects), at least one inquiry is answered based on information contained within the identifier of the computer system security event.

In a ninth aspect according to any of the previous aspects (e.g., the first through eighth aspects), at least one inquiry is answered based on the result of a computing process associated with the subset of the plurality of questions.

In a tenth aspect according to any of the previous aspects (e.g., the first through ninth aspects), the intervention includes at least one of generating a security alert, presenting a two factor authentication challenge, and/or blocking network traffic.

In an eleventh aspect according to any of the previous aspects (e.g., the first through tenth aspects aspects), the computer system security event occurred on at least one of a single computing device, a plurality of computing devices, a distributed computing process, and/or a computing network.

In a twelfth aspect, a system is provided that includes a processor and a memory. The memory stores instructions which, when executed by the processor, cause the processor to receive an identifier of a computer system security event and sequentially process a plurality of inquiries. Subsequent inquiries in the plurality of inquiries may be selected and asked based on responses to earlier inquiries in the plurality of inquiries. The instructions may further cause the processor to store indications of (i) the plurality of inquiries processed and (ii) responses received to the plurality of inquiries into a tensor and determine, with a machine learning model, that the tensor identifies a potential computer system security breach. The instructions may also cause the processor to generate an intervention for the potential computer system security breach.

In a thirteenth aspect according to any of the previous aspects (e.g., the twelfth aspect), at least a first inquiry of the plurality of inquiries identifies subsequent inquiries based on the response received to the first inquiry.

In a fourteenth aspect according to any of the previous aspects (e.g., the twelfth and thirteenth aspects), the inquiries are selected from a larger set of inquiries.

In a fifteenth aspect according to any of the previous aspects (e.g., the twelfth through fourteenth aspects), the tensor has rows for each of the larger set of inquiries.

In a sixteenth aspect according to any of the previous aspects (e.g., the twelfth through fifteenth aspects), the tensor contains null data values for rows corresponding to inquiries from the larger set of inquiries that are not contained in the plurality of inquiries.

In a seventeenth aspect according to any of the previous aspects (e.g., the twelfth through sixteenth aspects), at least a subset of the plurality of inquiries are answered manually.

In an eighteenth aspect according to any of the previous aspects (e.g., the twelfth through seventeenth aspects), at least a subset of the plurality of inquiries are answered automatically.

In a nineteenth aspect according to any of the previous aspects (e.g., the twelfth through eighteenth aspects), at least one inquiry is answered based on information contained within the identifier of the computer system security event.

In a twentieth aspect according to any of the previous aspects (e.g., the twelfth through nineteenth aspects), at least one inquiry is answered based on the result of a computing process associated with the subset of the plurality of questions.

In a twenty-first aspect according to any of the previous aspects (e.g., the twelfth through twentieth aspects), the intervention includes at least one of: generating a security alert, presenting a two factor authentication challenge, and/or blocking network traffic.

In a twenty-second aspect according to any of the previous aspects (e.g., the twelfth through twenty-first aspects), the computer system security event occurred on at least one of a single computing device, a plurality of computing devices, a distributed computing process, and/or a computing network.

In a twenty-third aspect, a non-transitory, computer-readable medium is provided storing instructions. When executed by a processor, the instructions may cause the processor to receive an identifier of a computer system security event and sequentially process a plurality of inquiries. Subsequent inquiries in the plurality of inquiries may be selected and asked based on responses to earlier inquiries in the plurality of inquiries. The instructions may further cause the processor to store indications of (i) the plurality of inquiries processed and (ii) responses received to the plurality of inquiries into a tensor and determine, with a machine learning model, that the tensor identifies a potential computer system security breach. The instructions may also cause the processor to generate an intervention for the potential computer system security breach.

In a twenty-fourth aspect, a system is provided that includes receiving means configured to receive an identifier of a computer system security event. The system may also include processing means configured to sequentially process a plurality of inquiries. Subsequent inquiries in the plurality of inquiries may be selected and asked based on responses to earlier inquiries in the plurality of inquiries. The system may further include storing means configured to store indications of (i) the plurality of inquiries processed and (ii) responses received to the plurality of inquiries into a tensor and determining means configured to determine, with a machine learning model, that the tensor identifies a potential computer system security breach. The system may still further include intervention means to generate an intervention for the potential computer system security breach.

In a twenty-fifth aspect, a method is provided that includes receiving an identifier of a medical event and sequentially processing a plurality of inquiries. Subsequent inquiries in the plurality of inquiries may be selected and asked based on responses to earlier inquiries in the plurality of inquiries. The method may also include storing indications of (i) the plurality of inquiries processed and (ii) responses received to the plurality of inquiries into a tensor and determining, with a machine learning model, that the tensor identifies a potential medical diagnosis. The method may further include generating an intervention for the potential medical diagnosis.

In a twenty-sixth aspect according to any of the previous aspects (e.g., the twenty-fifth aspect), at least a first inquiry of the plurality of inquiries identifies subsequent inquiries based on the response received to the first inquiry.

In a twenty-seventh aspect according to any of the previous aspects (e.g., the twenty-fifth and twenty-sixth aspects), the inquiries are selected from a larger set of inquiries.

In a twenty-eighth aspect according to any of the previous aspects (e.g., the twenty-fifth through twenty-seventh aspects), the tensor has rows for each of the larger set of inquiries.

In a twenty-ninth aspect according to any of the previous aspects (e.g., the twenty-fifth through twenty-eighth aspects), the tensor contains null data values for rows corresponding to inquiries from the larger set of inquiries that are not contained in the plurality of inquiries.

In a thirtieth aspect according to any of the previous aspects (e.g., the twenty-fifth through twenty-ninth aspects), at least a subset of the plurality of inquiries are answered manually.

In a thirty-first aspect according to any of the previous aspects (e.g., the twenty-fifth through thirtieth aspects), at least a subset of the plurality of inquiries are answered automatically.

In a thirty-second aspect according to any of the previous aspects (e.g., the twenty-fifth through thirty-first aspects), at least one inquiry is answered based on information contained within the identifier of the medical event.

In a thirty-third aspect according to any of the previous aspects (e.g., the twenty-fifth through thirty-second aspects), at least one inquiry is answered based on the result of a computing process associated with the subset of the plurality of inquiries.

In a thirty-fourth aspect, a system is provided that includes a processor and a memory. The memory may store instructions which, when executed by the processor, cause the processor to receive an identifier of a medical event and sequentially process a plurality of inquiries. Subsequent inquiries in the plurality of inquiries may be selected and asked based on responses to earlier inquiries in the plurality of inquiries. The instructions may also cause the processor to store indications of (i) the plurality of inquiries processed and (ii) responses received to the plurality of inquiries into a tensor and determine, with a machine learning model, that the tensor identifies a potential medical diagnosis. The instructions may further cause the processor to generate an intervention for the potential medical diagnosis.

In a thirty-fifth aspect according to any of the previous aspects (e.g., the thirty-fourth aspect), at least a first inquiry of the plurality of inquiries identifies subsequent inquiries based on the response received to the first inquiry.

In a thirty-sixth aspect according to any of the previous aspects (e.g., the thirty-fourth and thirty-fifth aspects), the inquiries are selected from a larger set of inquiries.

In a thirty-seventh aspect according to any of the previous aspects (e.g., the thirty-fourth through thirty-sixth aspects), the tensor has rows for each of the larger set of inquiries.

In a thirty-eighth aspect according to any of the previous aspects (e.g., the thirty-fourth through thirty-seventh aspects), the tensor contains null data values for rows corresponding to inquiries from the larger set of inquiries that are not contained in the plurality of inquiries.

In a thirty-ninth aspect according to any of the previous aspects (e.g., the thirty-fourth through thirty-eighth aspects), at least a subset of the plurality of inquiries are answered manually.

In a fortieth aspect according to any of the previous aspects (e.g., the thirty-fourth through thirty-ninth aspects), at least a subset of the plurality of inquiries are answered automatically.

In a forty-first aspect according to any of the previous aspects (e.g., the thirty-fourth through fortieth aspects), at least one inquiry is answered based on information contained within the identifier of the medical event.

In a forty-second aspect according to any of the previous aspects (e.g., the thirty-fourth through forty-first aspects), at least one inquiry is answered based on the result of a computing process associated with the subset of the plurality of questions.

In a forty-third aspect, a non-transitory, computer-readable medium is provided storing instructions. When executed by a processor, the instructions may cause the processor to receive an identifier of a medical event and sequentially process a plurality of inquiries. Subsequent inquiries in the plurality of inquiries may be selected and asked based on responses to earlier inquiries in the plurality of inquiries. The instructions may also cause the processor to store indications of (i) the plurality of inquiries processed and (ii) responses received to the plurality of inquiries into a tensor and determine, with a machine learning model, that the tensor identifies a potential medical diagnosis. The instructions may further cause the processor to generate an intervention for the potential medical diagnosis.

In a forty-fourth aspect, a system is provided that includes receiving means configured to receive an identifier of a medical event. The system may also include processing means configured to sequentially process a plurality of inquiries. Subsequent inquiries in the plurality of inquiries may be selected and asked based on responses to earlier inquiries in the plurality of inquiries. The system may further include storage means configured to store indications of (i) the plurality of inquiries processed and (ii) responses received to the plurality of inquiries into a tensor. The system may still further include determining means configured to determine, with a machine learning model, that the tensor identifies a potential medical diagnosis. The system may also include intervention means configured to generate an intervention for the potential medical diagnosis.

To the extent that any of these aspects are mutually exclusive, it should be understood that such mutual exclusivity shall not limit in any way the combination of such aspects with any other aspect whether or not such aspect is explicitly recited. Any of these aspects may be claimed, without limitation, as a system, method, apparatus, device, medium, etc.

All of the disclosed methods and procedures described in this disclosure can be implemented using one or more computer programs or components. These components may be provided as a series of computer instructions on any conventional computer readable medium or machine readable medium, including volatile and non-volatile memory, such as RAM, ROM, flash memory, magnetic or optical disks, optical memory, or other storage media. The instructions may be provided as software or firmware, and may be implemented in whole or in part in hardware components such as ASICs, FPGAs, DSPs, or any other similar devices. The instructions may be configured to be executed by one or more processors, which when executing the series of computer instructions, performs or facilitates the performance of all or part of the disclosed methods and procedures.

It should be understood that various changes and modifications to the examples described here will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A method comprising:
    receiving an identifier of a computer system security event;
    sequentially processing a plurality of inquiries, wherein subsequent inquiries in the plurality of inquiries are selected and processed based on responses to earlier inquiries in the plurality of inquiries;
    storing indications of (i) the plurality of inquiries processed and (ii) responses received to the plurality of inquiries into a tensor;
    determining, with a machine learning model, that the tensor identifies a potential computer system security breach; and
    generating an intervention for the potential computer system security breach.

2. The method of claim 1, wherein at least a first inquiry of the plurality of inquiries identifies subsequent inquiries based on the response received to the first inquiry.

3. The method of claim 1, wherein the inquiries are selected from a larger set of inquiries.

4. The method of claim 3, wherein the tensor has rows for each of the larger set of inquiries.

5. The method of claim 4, wherein the tensor contains null data values for rows corresponding to inquiries from the larger set of inquiries that are not contained in the plurality of inquiries.

6. The method of claim 1, wherein at least a subset of the plurality of inquiries are answered manually.

7. The method of claim 1, wherein at least a subset of the plurality of inquiries are answered automatically.

8. The method of claim 7, wherein at least one inquiry is answered based on information contained within the identifier of the computer system security event.

9. The method of claim 7, wherein at least one inquiry is answered based on a result of a computing process associated with the subset of the plurality of inquiries.

10. The method of claim 1, wherein the intervention includes at least one of: generating a security alert, presenting a two factor authentication challenge, and/or blocking network traffic.

11. The method of claim 1, wherein the computer system security event occurred on at least one of a single computing device, a plurality of computing devices, a distributed computing process, and/or a computing network.

12. A system comprising:
    a processor; and
    a memory storing instructions which, when executed by the processor, cause the processor to:
        receive an identifier of a computer system security event;
        sequentially process a plurality of inquiries, wherein subsequent inquiries in the plurality of inquiries are selected and processed based on responses to earlier inquiries in the plurality of inquiries;
        store indications of (i) the plurality of inquiries processed and (ii) responses received to the plurality of inquiries into a tensor;
        determine, with a machine learning model, that the tensor identifies a potential computer system security breach; and
        generate an intervention for the potential computer system security breach.

13. The system of claim 12, wherein at least a first inquiry of the plurality of inquiries identifies subsequent inquiries based on the response received to the first inquiry.

14. The system of claim 12, wherein the inquiries are selected from a larger set of inquiries.

15. The system of claim 14, wherein the tensor has rows for each of the larger set of inquiries.

16. The system of claim 15, wherein the tensor contains null data values for rows corresponding to inquiries from the larger set of inquiries that are not contained in the plurality of inquiries.

17. The system of claim 12, wherein at least a subset of the plurality of inquiries are answered manually.

18. The system of claim 12, wherein at least a subset of the plurality of inquiries are answered automatically.

19. The system of claim 18, wherein at least one inquiry is answered based on information contained within the identifier of the computer system security event.

20. A non-transitory, computer-readable medium storing instructions which, when executed by a processor, cause the processor to:
    receive an identifier of a computer system security event;
    sequentially process a plurality of inquiries, wherein subsequent inquiries in the plurality of inquiries are selected and processed based on responses to earlier inquiries in the plurality of inquiries;
    store indications of (i) the plurality of inquiries processed and (ii) responses received to the plurality of inquiries into a tensor;
    determine, with a machine learning model, that the tensor identifies a potential computer system security breach; and
    generate an intervention for the potential computer system security breach.

* * * * *